United States Patent
Haji Reza et al.

(10) Patent No.: US 10,327,646 B2
(45) Date of Patent: *Jun. 25, 2019

(54) NON-INTERFEROMETRIC PHOTOACOUSTIC REMOTE SENSING (NI-PARS)

(71) Applicant: ILLUMISONICS INC., Edmonton, Alberta (CA)

(72) Inventors: Parsin Haji Reza, Edmonton (CA); Roger Zemp, Edmonton (CA)

(73) Assignee: illumiSonics Inc., Edmonton, Alberta ( * ) Notice: Subject to any disclaimer, the term of this patent is extended or adjusted under 35 U.S.C. 154(b) by 0 days.

This patent is subject to a terminal disclaimer.

(21) Appl. No.: 15/418,447

(22) Filed: Jan. 27, 2017

(65) Prior Publication Data
US 2017/0215738 A1 Aug. 3, 2017

Related U.S. Application Data

(60) Provisional application No. 62/290,275, filed on Feb. 2, 2016.

(51) Int. Cl.
*G01N 21/17* (2006.01)
*A61B 5/00* (2006.01)

(52) U.S. Cl.
CPC ....... *A61B 5/0095* (2013.01); *G01N 21/1702* (2013.01); *G01N 2021/1725* (2013.01)

(58) Field of Classification Search
CPC .... A61B 5/0095; A61B 1/07; G01N 21/1702; G01N 21/4133; G01N 21/1717; G01N 2201/0846; G01N 2201/06113
USPC ......................................... 356/432, 630–632
See application file for complete search history.

(56) References Cited

U.S. PATENT DOCUMENTS

| | | | |
|---|---|---|---|
| 5,070,733 A | 12/1991 | Nagata et al. | |
| 5,479,259 A | 12/1995 | Nakata et al. | |
| 5,615,675 A * | 4/1997 | O'Donnell | G01N 29/0681 600/425 |
| 5,991,479 A * | 11/1999 | Kleinerman | G01J 5/08 250/227.11 |

(Continued)

FOREIGN PATENT DOCUMENTS

| CN | 101526483 A | 9/2009 |
|---|---|---|
| WO | 2009055705 A3 | 4/2009 |

(Continued)

OTHER PUBLICATIONS

Beard, P., "Biomedical Photoacoustic Imaging," Interface Focus 1.4 (2011), <http://www.rsfs.royalsocietypublishing.org> [retrieved Dec. 11, 2017], pp. 1-30.

*Primary Examiner* — Isiaka O Akanbi
(74) *Attorney, Agent, or Firm* — Bookoff McAndrews, PLLC

(57) ABSTRACT

A photoacoustic remote sensing system (NI-PARS) for imaging a subsurface structure in a sample, has an excitation beam configured to generate ultrasonic signals in the sample at an excitation location; an interrogation beam incident on the sample at the excitation location, a portion of the interrogation beam returning from the sample that is indicative of the generated ultrasonic signals; an optical system that focuses at least one of the excitation beam and the interrogation beam with a focal point that is below the surface of the sample; and a detector that detects the returning portion of the interrogation beam.

21 Claims, 8 Drawing Sheets

(56) References Cited

U.S. PATENT DOCUMENTS

| | | | |
|---|---|---|---|
| 6,016,202 A * | 1/2000 | Fuchs | G01B 11/06 |
| | | | 356/432 |
| 6,078,397 A | 6/2000 | Monchalin et al. | |
| 6,256,100 B1 * | 7/2001 | Banet | G01B 11/0666 |
| | | | 356/432 |
| 8,004,689 B2 * | 8/2011 | Monchalin | G01N 21/1702 |
| | | | 356/502 |
| 8,180,134 B2 | 5/2012 | Wang | |
| 8,454,512 B2 | 6/2013 | Wang et al. | |
| 9,153,931 B2 | 10/2015 | Ichihara et al. | |
| 2006/0184042 A1 | 8/2006 | Wang et al. | |
| 2006/0262316 A1 | 11/2006 | Baney | |
| 2009/0170149 A1 | 7/2009 | Viator et al. | |
| 2010/0268042 A1 * | 10/2010 | Wang | A61B 5/0059 |
| | | | 600/322 |
| 2011/0022328 A1 * | 1/2011 | Granot | G01N 21/359 |
| | | | 702/19 |
| 2012/0200845 A1 * | 8/2012 | Rousseau | G01N 21/1702 |
| | | | 356/72 |
| 2012/0320368 A1 | 12/2012 | Jiao et al. | |
| 2014/0118749 A1 | 5/2014 | Nakajima et al. | |
| 2014/0185055 A1 * | 7/2014 | Wang | A61B 5/0066 |
| | | | 356/479 |
| 2014/0247456 A1 | 9/2014 | Horstmann et al. | |
| 2015/0148655 A1 | 5/2015 | Haupt et al. | |
| 2015/0150465 A1 | 6/2015 | Irisawa et al. | |
| 2015/0153269 A1 | 6/2015 | Nakatsuka | |
| 2015/0164337 A1 | 6/2015 | Kim et al. | |
| 2015/0185187 A1 | 7/2015 | Wang et al. | |
| 2015/0221081 A1 | 8/2015 | Chang et al. | |
| 2015/0265156 A1 | 9/2015 | Tanaka | |
| 2016/0095520 A1 * | 4/2016 | Zhang | A61B 5/7242 |
| | | | 600/407 |

FOREIGN PATENT DOCUMENTS

| | | |
|---|---|---|
| WO | 2014027316 A2 | 2/2014 |
| WO | 2014062529 A1 | 4/2014 |
| WO | 2014160116 A1 | 10/2014 |
| WO | 2014168930 A1 | 10/2014 |

* cited by examiner

NON-INTERFEROMETRIC PHOTOACOUSTIC REMOTE SENSING (NI-PARS)

FIELD

This relates to the field of biomedical optics imaging and, in particular, to a laser and ultrasound-based method and system for in vivo or ex vivo, non-contact imaging of biological tissue.

BACKGROUND

Photoacoustic imaging is an emerging hybrid imaging technology providing optical contrast with high spatial resolution. Nanosecond or picosecond laser pulses fired into tissue launch thermo-elastic-induced acoustic waves which are detected and reconstructed to form high-resolution images. Photoacoustic imaging has been developed into multiple embodiments, including photoacoustic tomography (PAT), photoacoustic microscopy (PAM), optical-resolution photoacoustic microscopy (OR-PAM), and array-based PA imaging (array-PAI). In photoacoustic tomography (PAT) signals are collected from multiple transducer locations and reconstructed to form a tomographic image in a way similar to X-ray CT. In PAM, typically, a single element focused high-frequency ultrasound transducer is used to collect photoacoustic signals. A photoacoustic signal as a function of time (depth) is recorded for each position in a mechanically scanned trajectory to form a 3-D photoacoustic image. The maximum amplitude as a function of depth can be determined at each x-y scan position to form a maximum amplitude projection (MAP) C-scan image. Photoacoustic microscopy has shown significant potential for imaging vascular structures from macro-vessels all the way down to micro-vessels. It has also shown great promise for functional and molecular imaging, including imaging of nanoparticle contrast agents and imaging of gene expression. Multi-wavelength photoacoustic imaging has been used for imaging of blood oxygen saturation, by using known oxy- and deoxy-hemoglobin molar extinction spectra.

In traditional photoacoustic imaging, spatial resolution is due to ultrasonic focusing and can provide a depth-to-resolution ratio greater than 100. In OR-PAM, penetration depth is limited to ~1 mm in tissue (due to fundamental limitations of light transport) but resolution is micron-scale due to optical focusing. OR-PAM can provide micron-scale images of optical absorption in reflection-mode, in vivo, something that no other technique can provide. OR-PAM is capable of imaging blood vessels down to capillary size noninvasively. Capillaries are the smallest vessels in the body and so much crucial biology occurs at this level, including oxygen and nutrient transport. Much can go wrong at the capillary level too. In cancers, cells have an insatiable appetite for oxygen and nutrients to support their uncontrolled growth. They invoke a range of signaling pathways to spawn new vessels in a process known as angiogenesis and these vessels typically form abnormally. Tumors are often highly heterogeneous and have regions of hypoxia. Photoacoustic imaging has demonstrated the ability to image blood oxygen saturation (SO2) and tumor hypoxia in vivo.

In most photoacoustic and ultrasound imaging systems, piezoelectric transducers have been employed, in which an ultrasound coupling medium such as water or ultrasound gel is required. However for many clinical applications such as wound healing, burn diagnostics, surgery, and many endoscopic procedures physical contact, coupling, or immersion is undesirable or impractical.

The detection of ultrasound in photoacoustic imaging has, until recently, relied on ultrasonic transducers in contact with the biological tissue or an ultrasonic coupling agent both of which have major drawbacks as described above. Some detection strategies to solving the non-contact optical interferometric sensing problems associated with photoacoustic imaging have been reported.

Optical means of detecting ultrasound and photoacoustic signals have been investigated over a number of years; however, to date no technique has demonstrated practical non-contact in vivo microscopy in reflection mode with confocal resolution and optical absorption as the contrast mechanism.

Most previous approaches detected surface oscillations with interferometric methods. Others used interferometry to observe photoacoustic stresses, including optical coherence tomography (OCT) methods. These methods offer potential sensitivity to the scattered probe beam phase modulations associated with motion of scatterers, subsurface and surface oscillations, as well as unwanted vibrations. They are also sensitive to complex amplitude reflectivity modulations.

One example of a low-coherence interferometry method for sensing photoacoustic signals was proposed in U.S. pregrant publication no. 2014/0185055 to be combined with an optical coherence tomography (OCT) system, resulting in 30 µm lateral resolution.

Another prior art system is described in U.S. pregrant publication no. 2012/0200845 entitled "Biological Tissue Inspection Method and System", which describes a noncontact photoacoustic imaging system for in vivo or ex vivo, non-contact imaging of biological tissue without the need for a coupling agent.

Other systems use a fiber based interferometer with optical amplification to detect photoacoustic signals and form photoacoustic images of phantoms with acoustic (not optical) resolution. However these systems suffer from a poor signal-to-noise ratio, other contact-based photoacoustic systems offer significantly improved detection capabilities, in vivo imaging was not demonstrated, and optical-resolution excitation was not demonstrated.

Industrial laser ultrasonics has used interferometry to detect acoustic signatures due to optical excitation of inanimate objects for non-destructive testing. This approach has been adapted to detect ultrasound ex vivo in chicken breast and calf brain specimens, however, optical-resolution focusing of the excitation light was not examined.

Laser Doppler vibrometry has been a powerful non-contact vibration sensing methodology, however, weak signal-to-noise and poor image quality have proven to be a limitation when sensing deep-tissue signals from broad-beam photoacoustic excitation.

Similarly, Mach Zehnder interferometry and two-wave mixing interferometry have been used previously for sensing photoacoustic signals. However many such techniques still require direct contact or fluid coupling; have not offered in vivo studies or optical resolution for phantom studies.

The non-interferometric photoacoustic remote sensing (NI-PARS) is fundamentally different from other approaches for detection ultrasound/photoacoustic signals. The system takes advantage of a pulsed excitation beam co-focused and co-scanned with an interrogation beam. The detection mechanism is based on a non-interferometric sensing. Rather than detecting surface oscillations, pressure-induced refractive-index modulation resulting from initial pressure fronts can be sampled right at their subsurface origin where acoustic pressures are large. The non-interferometric nature of detection along with the short-coherence lengths of the interrogation laser preclude detection of surface- and subsurface oscillations to provide only the initial pressure signals.

SUMMARY

According to an aspect, there is provided a non-interferometric photoacoustic remote sensing system (NI-PARS) for imaging a subsurface structure in a sample, where the NI-PARS comprises an excitation beam configured to generate ultrasonic signals in the sample at an excitation location; an interrogation beam incident on the sample at the excitation location, a portion of the interrogation beam returning from the sample that is indicative of the generated ultrasonic signals; an optical system that focuses the excitation beam at a first focal point and the interrogation beam at a second focal point, the first and second focal points being below the surface of the sample; and an optical detector to detect the returning portion of the interrogation beam.

According to another aspect, there is provided an endoscopic device that uses a non-interferometric photoacoustic remote sensing system (NI-PARS) for imaging a subsurface structure in a sample, the endoscopic device comprising a fiber optic cable having an input end and a detection end; an excitation beam coupled to the input end of the fibre optic cable, wherein in use the excitation beam generates ultrasonic signals in the sample at an excitation location that is adjacent to the detection end of the fiber optic cable, the fiber optic cable focusing the excitation beam at a first focal point that is below the surface of the sample; an interrogation beam coupled to the input end of the fibre optic cable and incident on the excitation location, the fiber optic cable focusing the excitation beam at a first focal point that is below the surface of the sample, and wherein a portion of the interrogation beam that is indicative of the generated ultrasonic signals is received by the detection end of the fiber optic cable and travels to the input end; and an optical detector that receives the returning portion of the interrogation beam at the input end of the fiber optic cable.

According to other aspects, either alone or in combination, as applicable: the first and second focal points may be within 1 mm of the surface of the sample; the first and second focal points may be greater than 1 µm below the surface of the sample; the focal point may be spaced below the surface of the sample at a depth that is greater than a focal zone of the respective at least one of the excitation beam and the interrogation beam; the excitation beam and the interrogation beam have a lateral separation of less than 1 mm or less than 0.5 mm on the sample; the excitation beam may have a focal point that is laterally within the focal zone of the interrogation beam; the interrogation beam may have a focal point that is laterally within the focal zone of the excitation beam; there may be a processor that calculates an image of the sample based on the returning portion of the interrogation beam; at least one of the first focal point and the second focal point may have a focal diameter of less than 30 µm, 10 µm, or 1 µm; the excitation beam may be scanned through the sample while the interrogation beam is stationary; the interrogation beam may be scanned through the sample while the excitation beam is stationary; and each of the interrogation beam and the excitation beam may be scanned through the sample concurrently.

The proposed NI-PARS approach intentionally eliminates phase-sensitivity due to interferometric detection to exclusively monitor intensity reflectivity changes.

In one aspect, the approach generates high initial photoacoustic pressures modify scattering properties, such as scattering cross section of individual particles or reflectivity from larger structures in the sample. This results in time-varying intensity reflectivity which does not require phase sensitive detection. Rejecting interferometric effects leads to high signal to noise ratio detection.

To observe such reflection modulations, the intensity changes of a probe beam in response to a generated photoacoustic initial pressure are measured. A non-interferometric approach with a low-coherence probe beam precludes any phase-modulation sensitivity to enable detection of intensity variations. The proposed approach transiently amplifies existing refractive index steps where absorption is present.

Other aspects will be apparent from the description and claims below.

BRIEF DESCRIPTION OF THE DRAWINGS

These and other features will become more apparent from the following description in which reference is made to the appended drawings, the drawings are for the purpose of illustration only and are not intended to be in any way limiting, wherein.

DESCRIPTION

Figure 1:
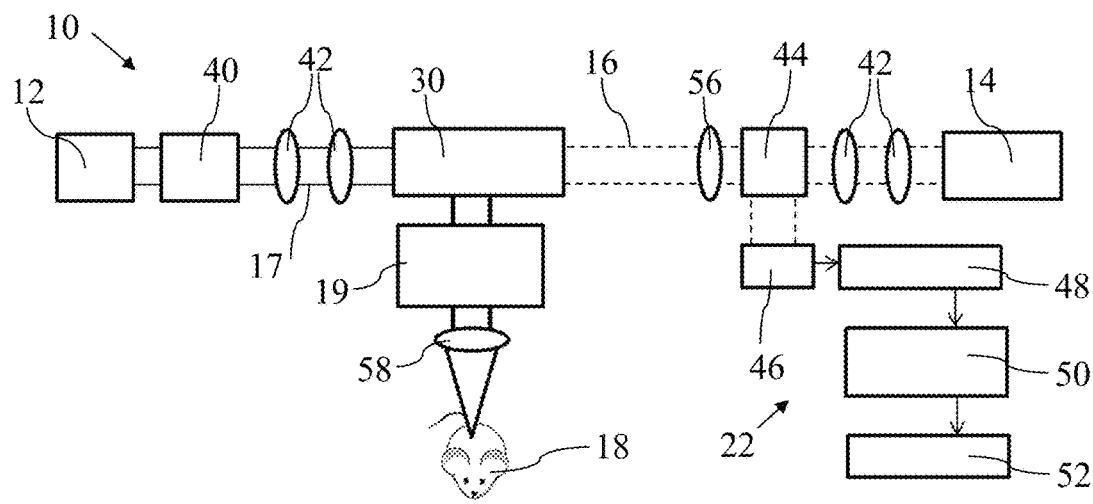
FIG. 1-FIG. 3 are the block diagram of non-interferometric photoacoustic remote sensing (NI-PARS) microscopy systems

Photoacoustic imaging is an emerging biomedical imaging modality that uses laser light to excite tissues. Energy absorbed by chromophores or any other absorber is converted to acoustic waves due to thermo-elastic expansion. These acoustic signals are detected and reconstructed to form images with optical absorption contrast. Photoacoustic imaging (PA) has been shown to provide exquisite images of microvessels and is capable of imaging blood oxygen saturation, gene expression, and contrast agents, among other uses. In most PA and ultrasound imaging systems piezoelectric transducers have been employed, in which an ultrasound coupling medium such as water or ultrasound gel is required. However for many clinical applications such as wound healing, burn diagnostics, surgery, and many endoscopic procedures physical contact, coupling, or immersion is undesirable or impractical. The system described herein is capable of in vivo optical-resolution photoacoustic microscopy using non-contact non-interferometric sensing without use of any ultrasound medium.

The system described herein, a non-interferometric photoacoustic remote sensing (NI-PARS) microscopy system, is based on the idea of focusing excitation light to a near diffraction-limited spot and detecting photoacoustic signals using a confocal interrogation beam co-focused with the excitation spot. While previous approaches for non-contact detection of photoacoustic signals used interferometry detection as well as a broad excitation beam with powerful lasers delivering mJ-J of pulse energy over a broad area, the NI-PARS microscopy technique described herein uses nJ-scale pulse energies focused to near diffraction-limited spots. When focusing into tissue, the surface fluence can be maintained below present ANSI limits for laser exposure but the ballistically-focused light beneath the tissue can create fluences transiently far above the ANSI limits (as is done in other microscopy methods). In NI-PARS, this means that very large local fluences ~J/cm$^2$ are created within a micronscale spot, generating very large initial acoustic pressures. For example, at 532-nm excitation wavelength, imaging a capillary with 500 mJ/cm$^2$ local fluence would result in an initial pressure on the order of 100 MPa locally. In NI-PARS approach, large optically-focused photoacoustic signals are detected as close to the photoacoustic source as possible, which is done optically by co-focusing an interrogation beam with the excitation spot.

The major difference of our proposed work with previously published systems is that a non-interferometric detection mechanism based on pressure-induced refractive-index modulation is used. Unlike interferometric methods, NI-PARS do not offer sensitivity to the scattered probe beam phase modulations associated with motion of scatterers, subsurface and surface oscillations, as well as unwanted vibrations. The net interferometric signal may be a mixture of these composite mechanisms and could lead to unwanted interference. A non-interferometric approach with a low-coherence probe beam precludes any phase-modulation sensitivity to enable detection of intensity variations. The proposed approach transiently amplifies existing refractive index steps where absorption is present. This generates a detectable change in the reflection characteristic of a sample. In the case of a surface much larger than the focal spot size of the detection beam this is a change in the intensity reflectivity of the surface. In the case of an object on the scale of, or smaller than, the detection focal spot size, this is a change in the scattering properties of the object. This in turn effects the back reflected collected fraction, or in the case of a large collection of small objects will affect the scattering properties of the excited medium.

Since we do not have to perform depth scanning, NI-PARS can perform near real time using a high pulse repetition laser and fast scanning mirrors. However, most previous non-contact photoacoustic detection methods have not shown real-time imaging capability and optical resolution was not demonstrated. We optically focus a pulsed excitation laser into superficial tissues to generate high microscale initial pressures. Then we harvest these large optically-focused photoacoustic signals as close to the photoacoustic source as possible. This is done by detecting photoacoustic signals using a confocal interrogation beam co-focused and co-scanned with the excitation spot. Local initial pressures are very large when optical focusing and thermal confinement conditions are applied. These large initial pressures can cause significant refractive index mismatch regions which are measured by the NI-PARS system as changes in reflected light.

To the best of our knowledge this is the first report on ultrasound/photoacoustic imaging detection mechanism based on pressure-induced refractive-index modulation as well as real-time non-contact detection. Our approach is the only method we know of to interrogate subsurface absorption with optical resolution using a non-contact system, aside from our previously disclosed interferometric PARS system, which however had a mixture of detection mechanisms, unlike the current method which only senses initial pressure at subsurface locations.

The high sensitivity and the fine resolution of the proposed system offer performance comparable to other in vivo optical resolution photoacoustic microscopy systems but in a non-contact reflection mode suitable for many clinical and pre-clinical applications.

Figure 2:
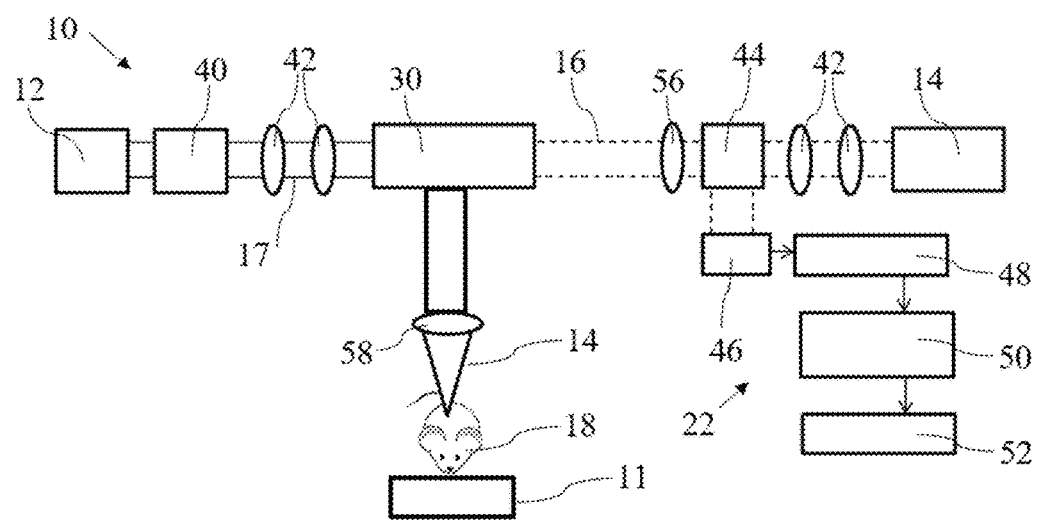
Figure 3:
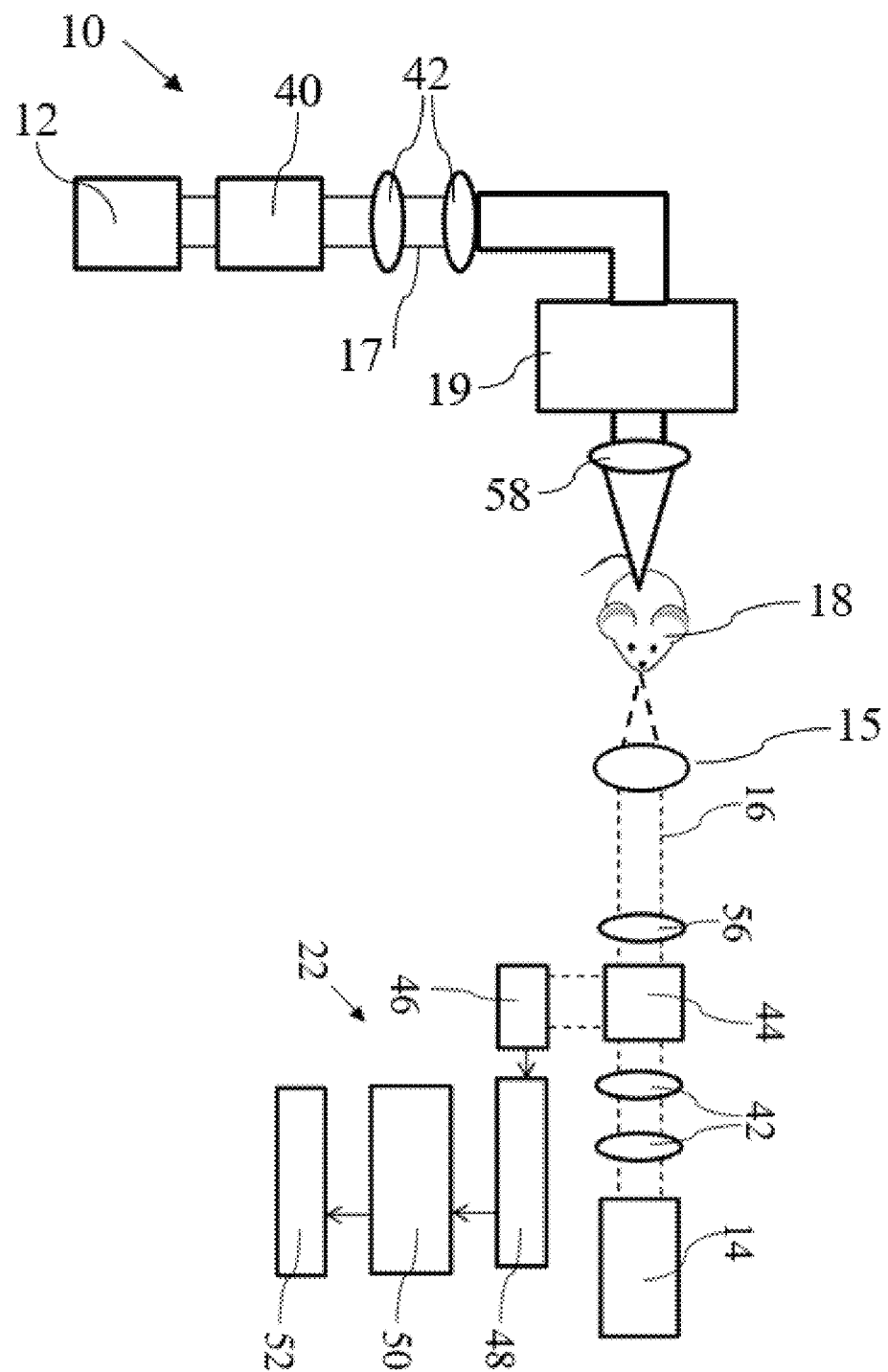

The general experimental setup of the non-interferometric optical-resolution photoacoustic remote sensing microscopy system are depicted through FIG. 1-3. Variations to the depicted system will be apparent to those skilled in the art. Referring to FIG. 1, a block diagram of NI-PARS system 10, and in particular, a non-interferometric optical-resolution photoacoustic remote sensing (NI-OR-PARS) microscopy system, is shown. A multi-wavelength fiber excitation laser 12 is used in multi focus form to generate photoacoustic signals. Excitation laser 12 preferably operates in the visible spectrum, although the particular wavelength may be selected according to the requirements of the particular application. The excitation beam 17 and interrogation beam 16 pass through a lens system 42 to adjust their focus on the sample 18. The excitation beam 17 will be combined with interrogation beam 16 using a beam combiner 30. The acoustic signatures are interrogated using either a short or long-coherence length probe beam 16 from a detection laser 14 that is co-focused and co-aligned with the excitation spots on sample 18. Interrogation/probe beam 16 passes through a polarizing beam splitter 44 and quarter wave plate 56 to guide the reflected light from sample 18 to the photodiode 46. The combined beam will be scanned by scanning unit 19. The scanning combined beams will pass through an objective lens 58 and focused on the sample 18. The reflected beam returns along the same path and is analyzed by detection unit 22. Unit 22 consists of amplifier 48, fast data acquisition card 50 and computer 52.

FIG. 2 shows the experimental setup on NI-PARS when the scanning unit 19 is replaced by scanning unit 11 in order to scan the sample 19 related to the to the fixed combined beams 14.

FIG. 3 shows an experimental setup that excitation and interrogation beams have separated path and are not combined. In this case the interrogation beam will be focused using another objective lens 15 to the sample 18.

In all the configurations, both beam can be scanned together. One beam can be fixed while the other beam can be scanned. The sample 18 can be scanned while both beam are fixed. The sample 18 can be scanned while both beam are scanning. The sample 18 can be scanned while one beam is fixed and the other is scanning.

It will be apparent that other examples may be designed with different components to achieve similar results. For example, other examples could include all-fiber architectures where circulators replace beam-splitters similar to optical-coherence tomography architectures. Other alternatives may include various coherence length sources, use of balanced photodetectors, interrogation-beam modulation, incorporation of optical amplifiers in the return signal path, etc.

The NI-PARS system takes advantage of two focused laser beams on the sample which can simulate a confocal NI-PAM configuration.

The NI-PARS takes advantage of optical excitation and detection which can help dramatically reduce the footprint of the system. The absence of a bulky ultrasound transducer makes this all optical system suitable for integrating with other optical imaging systems. Unlike many previous non-contact photoacoustic imaging systems, the NI-PARS system is capable of in vivo imaging. It relies on much simpler setup and takes advantage of recording the large initial ultrasound pressures without appreciable acoustic loses.

During in vivo imaging experiments, no agent or ultrasound coupling medium are required. However the target can be prepared with water or any liquid such as oil before non-contact imaging session. NI-PARS does not require a floating table unlike many other interferometric sensors. No special holder or immobilization is required to hold the target during imaging sessions.

Other advantages that are inherent to the structure will be apparent to those skilled in the art. The embodiments described herein are illustrative and not intended to limit the scope of the claims, which are to be interpreted in light of the specification as a whole.

A pulse laser is used to generate photoacoustic signals and the acoustic signatures are interrogated using either a long-coherence or short-coherence length probe beam co-focused with the excitation spots. The NI-PARS system is utilized to remotely record the large local initial pressures from chromophores and without appreciable acoustic loses due to diffraction, propagation and attenuation.

The excitation beam may be any pulsed or modulated source of electromagnetic radiation including lasers or other optical sources. In one example, a nanosecond-pulsed laser was used. The excitation beam may be set to any wavelength suitable for taking advantage of optical (or other electromagnetic) absorption of the sample. The source may be monochromatic or polychromatic.

The interrogation beam may be any pulsed, continues or modulated source of electromagnetic radiation including lasers or other optical sources. Any wavelength can be sued for interrogation purpose depends on the application.

The chromatic aberration in the collimating and objective lens pair was harnessed to refocus light from a fiber into the object so that each wavelength is focused at a slightly different depth location. Using these wavelengths simultaneously was previously shown to improve the depth of field and SNR for structural imaging of microvasculature with OR-PAM.

Since the design is not interferometric, the probe/receiver/interrogation beam, may be a long-coherence or a short-coherence length probe beam. Without need of any reference beam or reference arm. Using a short-coherence length, however, may ensure preclusion of interference from reflections in the system or sample to avoid unwanted signals and to extract only photoacoustic initial pressures.

Unlike optical coherence tomography (OCT) or interferometry detection of photoacoustic signal, the NI-PARS system detects the changes in the amount of the reflected light from sample due to acoustic pressure and no interferometry design such as, reference beam, reference arm or axial scanning of reference beam are needed.

NI-PARS may be integrated with OCT to provide a complete set of information offered by both photoacoustic and OCT systems.

NI-PARS with a short or long-coherence beam may be used for either optical resolution photoacoustic microscopy (OR-PAM) or common photoacoustic microscopy (PAM).

In one example, both excitation and receiver beam may be combined and scanned. In this way, photoacoustic excitations may be sensed in the same area as they are generated and where they are the largest. Other arrangements may also be used, including keeping the receiver beam fixed while scanning the excitation beam or vice versa. Galvanometers, MEMS mirrors and stepper/DC motors may be used as a means of scanning the excitation beam, probe/receiver beam or both.

The configurations shown in FIG. 4a-4d may be used to perform NI-PARS imaging.

Figure 4A:
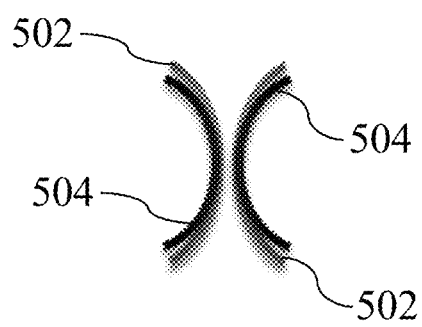
FIG. 4a-4d are representative drawings of the overlap between the exciter and interrogator beams on a sample.
Figure 4B:
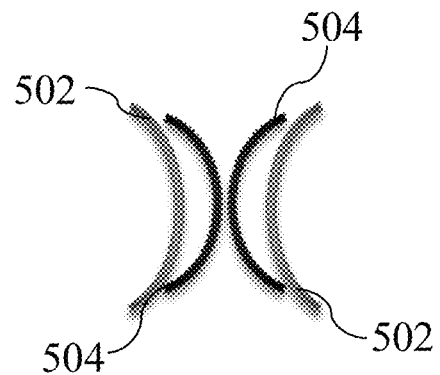
Figure 4C:
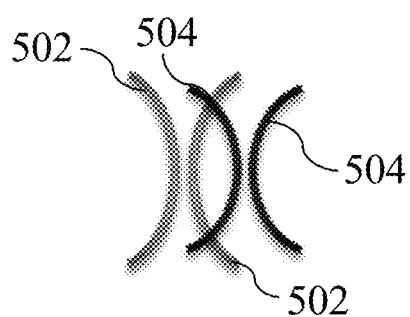
Figure 4D:
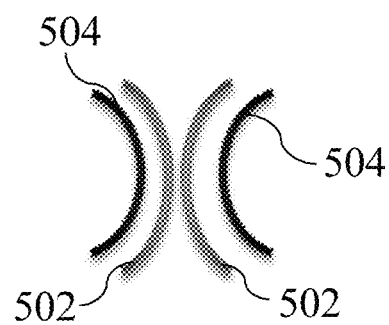
Figure 5A:
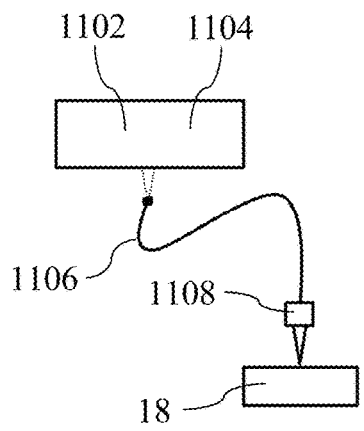
FIG. 5a-5c are block diagrams of examples of sensing systems in an endoscopy configuration.
Figure 5B:
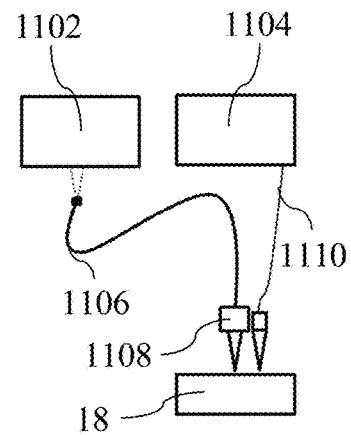
Figure 5C:
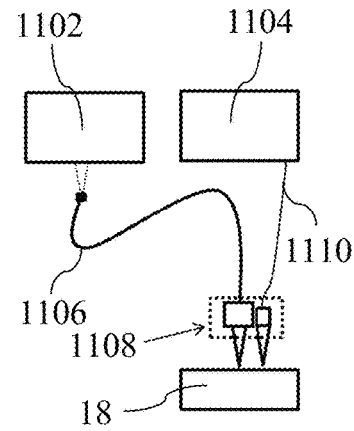

In the depicted embodiments, lines 502, depicted with a larger radius of curvature, represent excitation beams and lines 504, depicted with a smaller radius of curvature, represent receiver beams. FIG. 5a offers a kind of confocal photoacoustic system where the excitation beam 502 and probing receive beam 504 are focused on the same spot, which can be on a micron- or sub-micron scale. In FIG. 5b, the optical resolution can be provided by the receiver beam 504, rather than the excitation beam 502. FIG. 5c shows excitation beam 502 and receiver beam 502 focused on different spots, and takes advantage of ultrasound time of flight in order to locate the excitation and receiver beams 502 and 504 at different positions. In FIG. 4d, optical resolution is provided by the excitation beam 502. Preferably, the focus of either or both of the excitation beam 502 or the detection beam 504 is less than 30 µm, less than 10 µm, less than 1 µm, or to the diffraction limit of light. A tighter focus results in a higher possible resolution and a better signal to noise ratio in the reflected beam that is detected. As used herein, the term "focus" is intended to refer to the focal zone of the beam, or the point at which the beam spot size is at the tightest size, and where the diameter of the focal zone is 30% greater than the diameter of the beam spot size. Also preferably, the excitation and detection beams 502 and 504 are focused on the same position, although there may be some spacing between the respective focuses as shown in FIG. 4c. In FIG. 4c, the beams may be focused at different locations, but preferably within 1 mm, 0.5 mm, 100 µm or within the range of the largest focus of the beam. In FIGS. 4a, 4b and 4d, the beams may be confocal, or may overlap within the focus of the beam with the largest focus. For example, in FIG. 4a, the excitation beam is larger than the detection beam, and the detection beam is directed at a location within the focus of the excitation beam. By moving the detection beam, the area within the excitation beam may be imaged. By having confocal beams, both beams may be moved to image the sample.

One or both of the beams are preferably focused below the surface of the sample. Generally speaking, the beams may be effectively focused up to 1 mm below the surface of the sample. The beams may be focused at least 1 µm below the surface, or focused such that focal point of the beam is at least the distance of focal zone of the beam below the surface of the sample. It will be understood that, while both beams are preferably focused below the surface, in some embodiments either the excitation beam or the interrogation beam may be focused below the surface, with the other focused on, for example, the surface of the sample. In cases where only one beam is focused below the surface of the sample, the separation between the beams discussed previously will be a lateral separation, i.e. in the plane of the sample and orthogonal to the depth of the sample.

The excitation beam and sensing/receiver beam can be combined using dichroic mirrors, prisms, beamsplitters, polarizing beamsplitters etc. They can also be focused using different optical paths.

The reflected light may be collected by photodiodes, avalanche photodiodes, phototubes, photomultipliers, CMOS cameras, CCD cameras (including EM-CCD, intensified-CCDs, back-thinned and cooled CCDs), etc. The detected light may be amplified by an RF amplifier, lock-in amplifier, trans-impedance amplifier, or other amplifier configuration. Also different methods may be used in order to filter the excitation beam from the receiver beam before detection. NI-PARS may use optical amplifiers to amplify detected light.

NI-PARS can be used in many form factors, such as table top, handheld and endoscopy. Examples of endoscopy NI-PARS are shown in FIGS. 5a, 5b and 5c with various arrangements of NI-PARS excitation units 1102, NI-PARS detection units 1104, fibre optics 1106 such as image-guide fibers, and lenses 1108 that focus the respective beams onto the sample 18. When excitation and detection units 1102 and 1104 are separated, there may be a separate fibre 1110 provided, such as a single mode fiber.

A table top and handheld NI-PARS system may be constructed based on principles known in the art. The proposed NI-PARS system takes advantage of optical excitation and detection which can help to dramatically reduce the footprint of the system. The footprint of previous systems has been much too large to use the system in all but body surfaces. For endoscopic applications, the footprint of the ultrasound detector must be minimized to make the imaging catheter small and flexible enough to navigate through small orifices and vessels. The piezoelectric receivers are not ideal candidates for endoscopic applications as there is trade-off between the sensitivity and the size of the receiver. On the other hand for many invasive applications sterilizable or disposable catheters and a non-contact approach are necessary. The system may also be used as NI-PARS endoscopy system with a potential footprint the size of an optical fiber, as both excitation and NI-PARS beam can be coupled into a single mode fiber or image guide fiber.

Image-guide fibers (miniaturized fiber bundles with as many as 100,000 or more individual micrometer-sized strands in a single optical fiber with diameters ranging from 200 μm to 2 mm) may be used to transmit both focused light spots. The excitation beam may be scanned either at the distal end or proximal end of the fiber using one of the scanning methods mentioned before. However, the receiver beam may be scanned or be fixed. The scanned spot is transmitted via the image-guide fiber 1106 to the output end. Therefore, it may be used to directly contact the sample, or re-focused using an attached miniature GRIN lens 1108. In one example, C-scan photoacoustic images were obtained from the fiber image-guides using an external ultrasound transducer to collect photoacoustic signals. Using an edge-spread and Gaussian function, a resolution of approximately 7 μm was obtained using the image-guide fiber 1106. It is believed that a higher resolution may also be obtained with appropriate improvements to the setup and equipment used.

Figure 6:
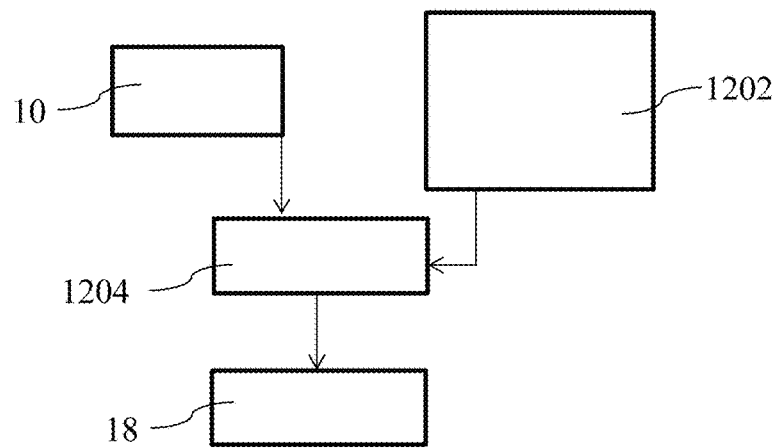
FIG. 6 is a block diagram of a sensing system integrated with another optical imaging system.

The NI-PARS system may be combined with other imaging modalities such as fluorescence microscopy, two-photon and confocal fluorescence microscopy, Coherent-Anti-Raman-Stokes microscopy, Raman microscopy, Optical coherence tomography, other photoacoustic and ultrasound systems, etc. This could permit imaging of the microcirculation, blood oxygenation parameter imaging, and imaging of other molecularly-specific targets simultaneously, a potentially important task that is difficult to implement with only fluorescence based microscopy methods. An example of a NI-PARS system 10 integrated with another optical imaging system 1202 is shown in FIG. 6, where NI-PARS 10 and the other optical imaging system 1202 are both connected to the sample 18 by a combiner 1204.

NI-PARS can be integrated with any interferometric designs for detection photoacoustic signals to extent its application. Interferometric designs such as common path interferometer (using specially designed interferometer objective lenses), Michelson interferometer, Fizeau interferometer, Ramsey interferometer, Sagnac interferometer, Fabry-Perot interferometer and Mach-Zehnder interferometer.

NI-PARS may be used for A, B or C scan images for in vivo, ex vivo or phantom studies.

A multi-wavelength visible laser source may also been implemented to generate photoacoustic signals for functional or structural imaging.

NI-PARS may be optimized in order to takes advantage of a multi-focus design for improving the depth-of-focus of 2D and 3D OR-NI-PARS imaging. The chromatic aberration in the collimating and objective lens pair may be harnessed to refocus light from a fiber into the object so that each wavelength is focused at a slightly different depth location. Using these wavelengths simultaneously may be used to improve the depth of field and signal to noise ratio (SNR) of NI-PARS images. During NI-PARS imaging, depth scanning by wavelength tuning may be performed.

Polarization analyzers may be used to decompose detected light into respective polarization states. The light detected in each polarization state may provide information about ultrasound-tissue interaction.

Applications

It will be understood that the system described herein may be used in various ways, such as those purposes described in the prior art, and also may be used in other ways to take advantage of the aspects described above. A non-exhaustive list of applications is discussed below.

The system may be used for imaging angiogenesis for different pre-clinical tumor models.

The system may also be used for clinical imaging of micro- and macro-circulation and pigmented cells, which may find use for applications such as in (1) the eye, potentially augmenting or replacing fluorescein angiography; (2) imaging dermatological lesions including melanoma, basal cell carcinoma, hemangioma, psoriasis, eczema, dermatitis, imaging Mohs surgery, imaging to verify tumor margin resections; (3) peripheral vascular disease; (4) diabetic and pressure ulcers; (5) burn imaging; (6) plastic surgery and microsurgery; (7) imaging of circulating tumor cells, especially melanoma cells; (8) imaging lymph node angiogenesis; (9) imaging response to photodynamic therapies including those with vascular ablative mechanisms; (10) imaging response to chemotherapeutics including anti-angiogenic drugs; (11) imaging response to radiotherapy.

The system may be useful in estimating oxygen saturation using multi-wavelength photoacoustic excitation and NI-PARS detection and applications including: (1) estimating venous oxygen saturation where pulse oximetry cannot be used including estimating cerebrovenous oxygen saturation and central venous oxygen saturation. This could potentially replace catheterization procedures which can be risky, especially in small children and infants.

Oxygen flux and oxygen consumption may also be estimated by using NI-PARS imaging to estimate oxygen saturation, and an auxiliary method to estimate blood flow in vessels flowing into and out of a region of tissue.

The system may also have some gastroenterological applications, such as imaging vascular beds and depth of invasion in Barrett's esophagus and colorectal cancers. Depth of invasion is key to prognosis and metabolic potential. Gastroenterological applications may be combined or piggy-backed off of a clinical endoscope and the miniaturized NI-PARS system may be designed either as a stand-alone endoscope or fit within the accessory channel of a clinical endoscope.

The system may have some surgical applications, such as functional imaging during brain surgery, use for assessment of internal bleeding and cauterization verification, imaging perfusion sufficiency of organs and organ transplants, imaging angiogenesis around islet transplants, imaging of skin-grafts, imaging of tissue scaffolds and biomaterials to evaluate vascularization and immune rejection, imaging to aid microsurgery, guidance to avoid cutting critical blood vessels and nerves.

Other examples of applications may include NI-PARS imaging of contrast agents in clinical or pre-clinical applications; identification of sentinel lymph nodes; non- or minimally-invasive identification of tumors in lymph nodes; imaging of genetically-encoded reporters such as tyrosinase, chromoproteins, fluorescent proteins for pre-clinical or clinical molecular imaging applications; imaging actively or passively targeted optically absorbing nanoparticles for molecular imaging; and imaging of blood clots and potentially staging the age of the clots.

NI-Pars Mechanism

Rather than calculate the phase shifts of transmitted light NI-PARS is interested in the light reflected from a refractive index mismatch. With a large initial pressure a significant refractive index step changes in the confined excitation volume occurs. This results in a large amplitude reflection coefficient. This mechanism will contribute to both amplitude and phase variations in the probe beam.

Refractive index changes from their unperturbed state can occur due to pressure rises. Initial pressures generated by the absorption of an optical excitation pulse which is shorter in time than the stress confinement and thermal confinement condition is described by $p_0 = \Gamma \phi \mu_a$ where $\Gamma$ is a material property known as the Grüneisen parameter, $\phi$ is the focal fluence of the excitation beam and $\mu_a$ is the optical absorption of the medium at the given excitation wavelength. These pressures can be large. As an example, assuming a focal fluence of 500 mJcm$^{-2}$, a whole blood sample (with a hemoglobin concentration of 150 gL$^{-1}$ assuming a fully oxygenated sample) with optical absorption at 532 nm excitation of 237 cm$^{-1}$ and a Grüneisen parameter of 1 gives an initial pressure of 119 MPa. These pressures are sufficient to create a measurable change in the refractive index which follows the elasto-optic relation such that the perturbed refractive index ($n^*(r,t)$) is related to the unperturbed refractive index ($n(r,t)$) and the pressure field ($p(r,t)$) by $n^*(r,t) = n[1 + (\eta n^2 p / 2\rho v_s^2)]$ where $\eta$ is the elasto-optic coefficient, $\rho$ is the specific density and $v_s$ is the speed of sound.

The accumulated phase shift of light passing through a zone of enhanced pressure can be calculated by Raman Nath diffraction theory and will depend on the direction of the sound and the direction of the light as well as the pressure field inhomogeneity. For a light beam incident on a plane pressure wave where both the light and sound beams are parallel, the accumulated phase shift should be zero and are rather maximum when sound fields create effective diffraction gratings orthogonal to the light propagation. The electric field back-reflected from the sample and incident on the photodiode is modelled as having two components, AC and DC terms ES=E(DC)+E(AC) Here E(DC) is the electric field magnitude of light reflected from the sample surface and E(AC) is the electric field amplitude of light reflected from the excitation volume beneath the surface due to a transient pressure induced optical index step. The fraction of light modulated compared to surface reflected light FP is calculated as FP=⟨|E(AC)|^2⟩/⟨|E(DC)|^2⟩. The fraction of modulated light due to pressure-induced refractive index change can be as significant of several percentage of the incident light.

When the sample consists of a planar interface (where the curvature of the surface is much larger than the probe beam focal spot size) the small changes in refractive index can produce changes in the reflectivity of the probe beam. This can be modeled by taking the difference in the intensity reflection coefficients of the perturbed $$\left( R^* = \left| \frac{n_1 + \delta n - n_2}{n_1 + \delta n + n_2} \right|^2 \right)$$

and unperturbed $$\left( R_s = \left| \frac{n_1 - n_2}{n_1 + n_2} \right|^2 \right)$$

interfaces such that the measured signal varies with amplitude following $\Delta R = R^* - R_s$ where $n_1$ is the refractive index of the optical absorbing medium and $n_2$ is the refractive index of the optically transparent medium. Assuming that the perturbation is small such that $\delta n \ll 1$; $\delta n \ll n_1$, $n_2$ and that the refractive indices are all mostly real (this is not a requirement, but merely allows for intuitive approximation) provides an expression following $$\Delta R = 4 \delta n R_s \frac{n_2}{n_1^2 - n_2^2} + \mathcal{O}\{\delta n\}$$

where o{δn} represents higher order terms. This describes a linear relationship with the static reflectivity (due to the initial refractive index mismatch between $n_1$ and $n_2$) and a linear relationship with the perturbation $\delta n$ which is in turn proportional to the photoacoustic initial pressure.

In the case of an object, or a collection of objects which are optically scattering, optically absorbing, and are on the scale of or smaller than the beam spot size, optical property changes are more appropriately described by scattering theory. The refractive index modulation brought on by the photoacoustic initial pressures now is assumed to alter the scattering properties of individual particles. For the case of single particle interactions this can be observed as a change in the collected fraction (or observed reflection) such that $\Delta R_c = R_c^* - R_{s,c}$ where $R_s^*$ is the modified collected fraction and $R_{s,c}$ is the unperturbed collected fraction. In brief these describe a relationship which follows $\Delta R_c \propto \Delta \sigma_s$ where $$\Delta\sigma_s = 2\delta n_s \sigma_s \left( \frac{n_s - n_b}{|n_s - n_b|^2} - 1 \right) + \mathcal{O}\{\delta n\}$$

is the change in the scattering cross-section of the particle, $n_s$ is the unperturbed refractive index of the particle, $\delta n_s$ is the refractive index change brought on by the elasto-optic effect, $n_b$ is the refractive index of the background medium and $\sigma_s$ is the unperturbed scattering cross section. In the case of a large ensemble of particles, the change in diffuse reflection is instead monitored which is described by radiative transfer theory in which individual particles are assumed to form an equivalent homogenous scattering medium with a perturbed and unperturbed set of optical scattering properties.

The system is sensitive to intensity reflectivity modulations at any depth within the probe beam optical depth-of-focus. Such modulations effectively begin instantaneously, coincident with the excitation pulse, irrespective of depth. Because the proposed system reads out phase-insensitive intensity reflectivity, time-resolved signals do not produce depth-resolved information.

Experimental Results

Figures 7A, 7B, 7C:
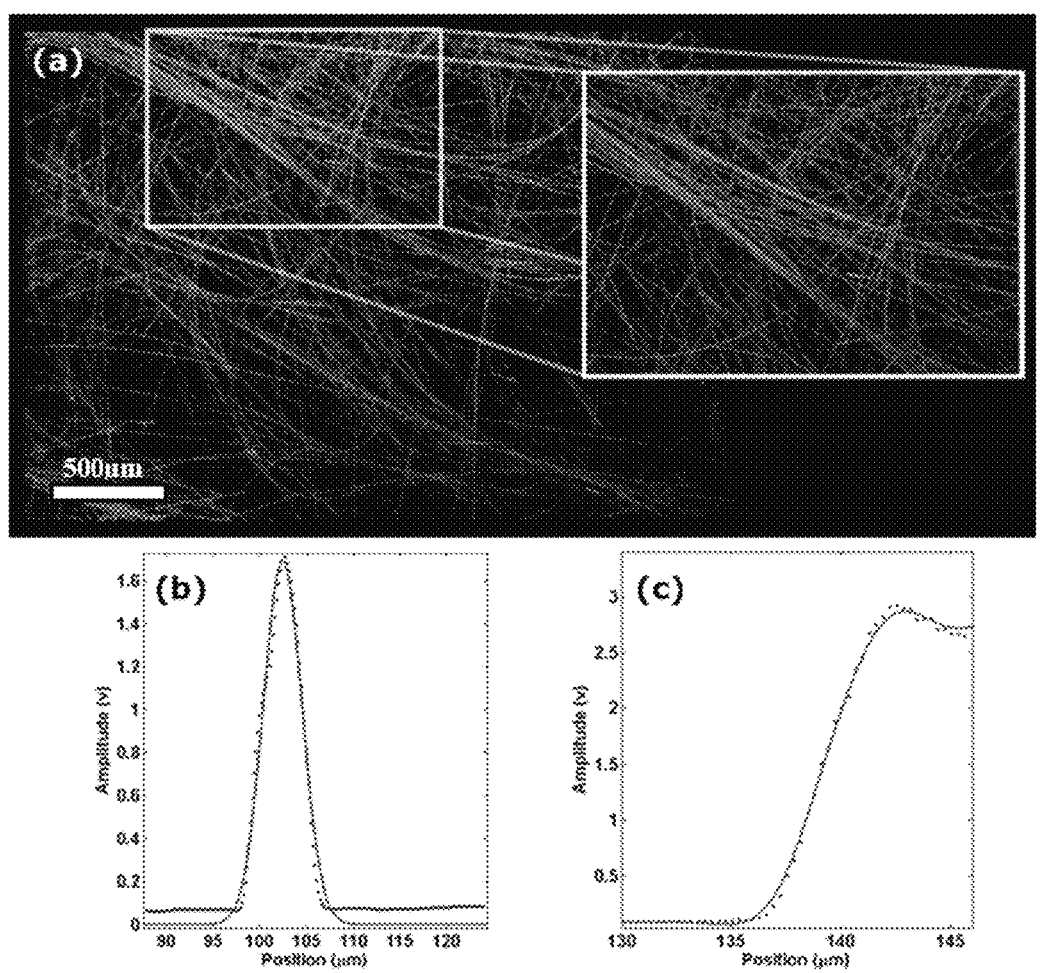
FIG. 7a is a NI-PARS image of a network of carbon fibres.
FIG. 7b is a graph of the FWHM obtained by fitting an individual carbon fiber signal amplitude to a Gaussian function.
FIG. 7c is a graph of the resolution using a knife edge spread function.

FIG. 7a shows NI-PARS (using experimental setup shown in FIG. 2) imaging of carbon fiber networks using ~1 nJ excitation pulse energy and 4 mW interrogation power. SNR (defined as average of signal over the standard deviation of the noise) was quantified as 45 dB. FIG. 7b shows FWHM due to fitting individual carbon fiber (with ~6 μm diameter) signal amplitude to a Gaussian function. FIG. 7c shows the resolution study using a knife edge spread function. The lateral resolution of the system has been measured as ~2.5±1 μm.

Figure 8:
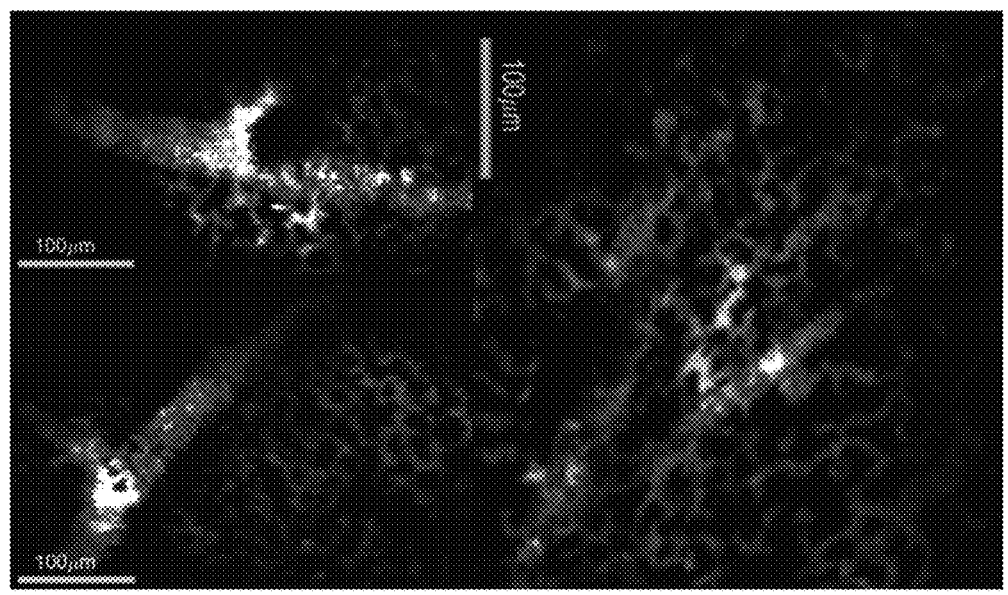
FIG. 8 in vivo images of CAM-membrane of 5-day chicken embryos.
Figure 9:
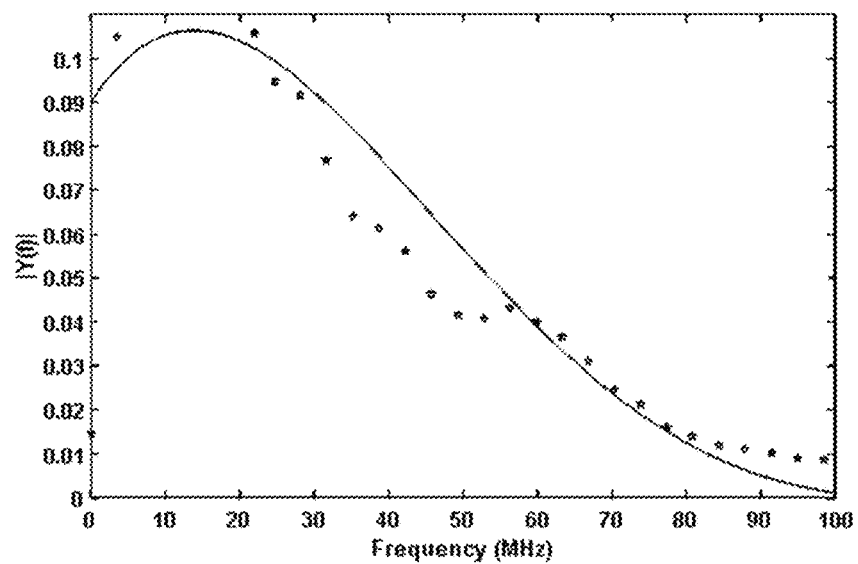
FIG. 9 depicts an example of the frequency response of a NI-PARS system.
Figure 10:
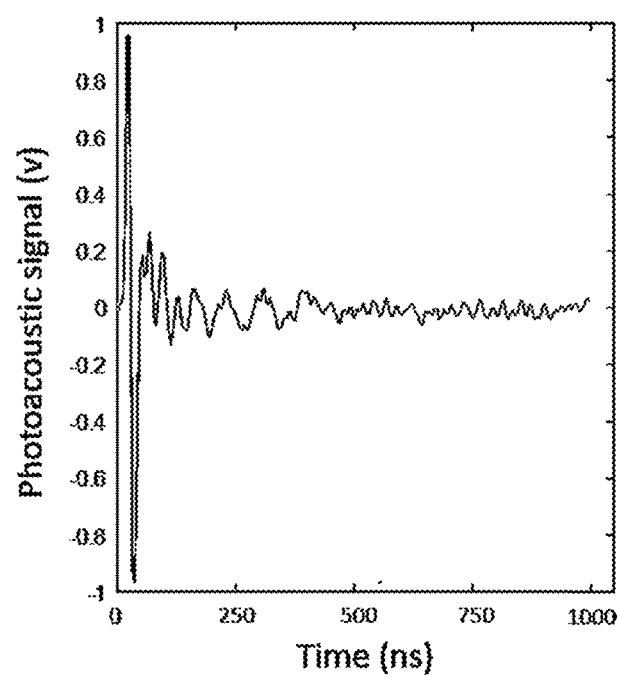
FIG. 10 depicts an example of the photoacoustic time domain signal of an individual carbon fiber using a NI-PARS system.

FIG. 8 show in vivo images of CAM-membrane of 5-day chicken embryos using the experimental setup shown in FIG. 1. FIG. 8 shows multi focus NI-PARS images revealing both capillary beds and bigger blood vessels. In the chicken embryo model bigger blood vessels usually are located deeper than capillaries. In order to see both deep- and shallow vessels simultaneously the multi-focus design is optimized to extend the depth-of-field to ~250 μm. A single wavelength can be used as well as shown in FIG. 7, However, with a single wavelength, depth-of-focus is limited to ~30 μm, rather than 250 μm with the multi-focus approach. Hence single-wavelength excitation is better-suited for depth-sectioning. FIG. 10 depicts the NI-PARS frequency response and FIG. 9 depicts the NI-PARS photoacoustic time domain signal of an individual carbon fiber.

Figure 11:
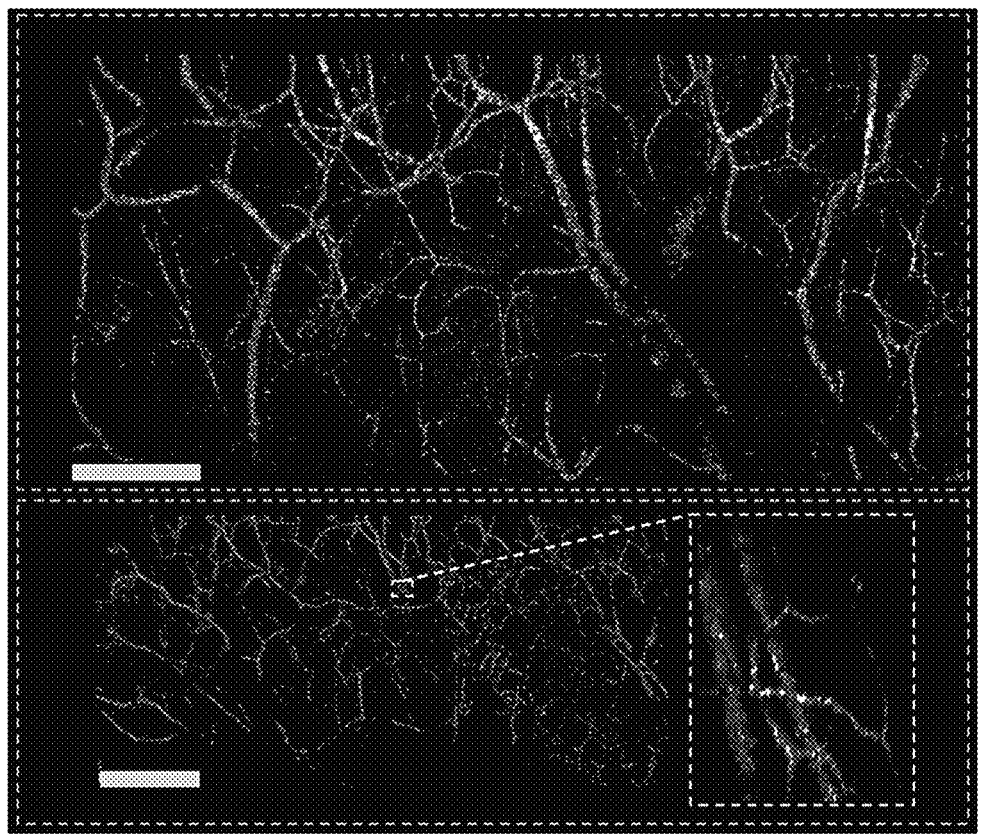
FIG. 11 depict in vivo NI-PARS images of a mouse ear.

FIG. 11 (using experimental setup shown in FIG. 1 and FIG. 2) depict in vivo NI-PARS images of a mouse ear. In all in vivo images pulse energy ~20-80 nJ was used and the interrogation power was fixed to 6 mW.

All the images shown herein are raw data and no major image processing steps are applied.

As will be understood, the high sensitivity and the fine resolution of the proposed system offer performance comparable to other in vivo optical resolution photoacoustic microscopy systems but with much higher signal to noise ratio and in a non-contact reflection mode suitable for many clinical and pre-clinical applications.

In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The scope of the following claims should not be limited by the preferred embodiments set forth in the examples above and in the drawings, but should be given the broadest interpretation consistent with the description as a whole.

The invention claimed is:

1. A non-interferometric photoacoustic remote sensing system (NI-PARS) for imaging a subsurface structure in a sample, comprising:
    one or more lasers configured to generate:
        a pulsed or intensity-modulated excitation beam configured to generate ultrasonic signals in the sample at an excitation location; and
        an interrogation beam incident on the sample at the excitation location, a portion of the interrogation beam returning from the sample that is indicative of the generated ultrasonic signals;
    an optical system that focuses the excitation beam and the interrogation beam below a surface of the sample;
    a non-interferometric detector that detects the returning portion of the interrogation beam; and
    a processor configured to calculate an image of the sample based on a detected intensity modulation of the returning portion of the interrogation beam from below the surface of the sample.

2. The NI-PARS of claim 1, wherein the excitation beam and the interrogation beam are focused within 1 mm of the surface of the sample.

3. The NI-PARS of claim 1, wherein at least one of the excitation beam and the interrogation beam is focused at a depth greater than 1 μm below the surface of the sample.

4. The NI-PARS of claim 1, wherein:
    the optical system focuses the excitation beam at a first focal point and the interrogation beam at a second focal point, the first and second focal points being below the surface of the sample; and
    at least one of the first and second focal points are spaced below the surface of the sample at a depth that is greater than a focal zone of the respective at least one of the excitation beam and the interrogation beam.

5. The NI-PARS of claim 4, wherein at least one of the first focal point and the second focal point has a focal diameter of less than 30 μm.

6. The NI-PARS of claim 1, wherein the excitation beam and the interrogation beam have a lateral separation of less than 1 mm within the sample.

7. The NI-PARS of claim 1, wherein the excitation beam has a focal point that is laterally within a focal zone of the interrogation beam; or the interrogation beam has a focal point that is laterally within a focal zone of the excitation beam.

8. The NI-PARS of claim 1, wherein:
    the excitation beam is scanned through the sample while the interrogation beam is stationary; or
    the interrogation beam is scanned through the sample while the excitation beam is stationary; or
    each of the interrogation beam and the excitation beam are scanned through the sample concurrently.

9. The NI-PARS of claim 1, wherein the interrogation beam is a continuous interrogation beam relative to the excitation beam; or the interrogation beam is a pulsed or modulated interrogation beam.

10. The NI-PARS of claim 1, wherein the sample is tissue.

11. The NI-PARS of claim 1, wherein the excitation beam and the interrogation beam are confocal.

12. The NI-PARS of claim 1, wherein:
the excitation beam has a first focus, and the interrogation beam has a second focus;
the excitation beam and the interrogation beam overlap within the first focus, when the first focus is larger than the second focus; and
the excitation beam and the interrogation beam overlap within the second focus, when the second focus is larger than the first focus.

13. The NI-PARS of claim 1, further including an additional imaging system selected from fluorescence microscopy, two-photon fluorescence microscopy, confocal fluorescence microscopy, Coherent-Anti-Raman-Stokes microscopy, Raman microscopy, optical coherence tomography, or other photoacoustic systems.

14. The NI-PARS of claim 1, wherein the processor is configured to estimate blood flow in vessels flowing into and out of a region of tissue.

15. The NI-PARS of claim 1, wherein the processor is configured to estimate oxygen saturation in the sample; or wherein the NI-PARS is used in one or more of the following applications:
   imaging angiogenesis for pre-clinical tumor models;
   estimating oxygen saturation using multi-wavelength photoacoustic excitation;
   estimating venous oxygen saturation where pulse oximetry cannot be used;
   estimating cerebrovenous oxygen saturation and/or central venous oxygen saturation;
   estimating oxygen flux and/or oxygen consumption;
   clinical imaging of micro- and macro-circulation and pigmented cells;
   imaging of the eye;
   augmenting or replacing fluorescein angiography;
   imaging dermatological lesions;
   imaging melanoma;
   imaging basal cell carcinoma;
   imaging hemangioma;
   imaging psoriasis;
   imaging eczema;
   imaging dermatitis;
   imaging Mohs surgery;
   imaging to verify tumor margin resections;
   imaging peripheral vascular disease;
   imaging diabetic and/or pressure ulcers;
   burn imaging;
   plastic surgery;
   microsurgery;
   imaging of circulating tumor cells;
   imaging melanoma cells;
   imaging lymph node angiogenesis;
   imaging response to photodynamic therapies;
   imaging response to photodynamic therapies having vascular ablative mechanisms;
   imaging response to chemotherapeutics;
   imaging response to anti-angiogenic drugs;
   imaging response to radiotherapy;
   imaging vascular beds and depth of invasion in Barrett's esophagus and/or colorectal cancers;
   functional imaging during brain surgery;
   assessment of internal bleeding and/or cauterization verification;
   imaging perfusion sufficiency of organs and/or organ transplants;
   imaging angiogenesis around islet transplants;
   imaging of skin-grafts;
   imaging of tissue scaffolds and/or biomaterials to evaluate vascularization and/or immune rejection;
   imaging to aid microsurgery;
   guidance to avoid cutting blood vessels and/or nerves;
   imaging of contrast agents in clinical or pre-clinical applications;
   identification of sentinel lymph nodes;
   non- or minimally-invasive identification of tumors in lymph nodes;
   imaging of genetically-encoded reporters, wherein the genetically-encoded reporters include tyrosinase, chromoproteins, and/or fluorescent proteins for pre-clinical or clinical molecular imaging applications;
   imaging actively or passively targeted optically absorbing nanoparticles for molecular imaging;
   imaging of blood clots; or
staging an age of blood clots.

16. The NI-PARS of claim 1, further including:
a polarizing beam splitter, wherein the interrogation beam is configured to pass through the polarizing beam splitter before reaching the sample; and
a quarter wave plate configured to guide the returning portion of the interrogation beam to the non-interferometric detector.

17. The NI-PARS of claim 1, wherein the system does not include an ultrasound transducer.

18. An endoscopic device that uses a photoacoustic remote sensing system (NI-PARS) for imaging a subsurface structure in a sample, the endoscopic device comprises:
   a fiber optic cable having an input end and a detection end;
   one or more lasers configured to generate:
      an excitation beam coupled to the input end of the fibre optic cable, wherein in use the excitation beam generates ultrasonic signals in the sample at an excitation location that is adjacent to the detection end of the fiber optic cable, the fiber optic cable focusing the excitation beam below a surface of the sample; and
      an interrogation beam coupled to the input end of the fibre optic cable and incident on the excitation location, the fiber optic cable focusing the excitation beam below the surface of the sample, and wherein a portion of the interrogation beam that is indicative of the generated ultrasonic signals is received by the detection end of the fiber optic cable and travels to the input end;
   a non-interferometric detector that receives the returning portion of the interrogation beam at the input end of the fiber optic cable; and
   a processor configured to calculate an image of the sample based on a detected intensity modulation of the returning portion of the interrogation beam from below the surface of the sample, wherein the intensity modulation is caused by the excitation beam focused below the surface of the sample.

19. The endoscopic device of claim 18, wherein the endoscopic device does not include an ultrasound transducer.

20. A non-interferometric photoacoustic remote sensing system (NI-PARS) for imaging a subsurface structure in a sample, comprising:
   one or more lasers configured to generate:
      a pulsed or intensity-modulated excitation beam configured to generate ultrasonic signals in the sample at an excitation location below a surface of the sample; and an interrogation beam incident on the sample at the excitation location, a portion of the interrogation beam returning from the sample that is indicative of the generated ultrasonic signals; wherein the one or more lasers include a single-wavelength source or a multi-wavelength source, an optical system that focuses the excitation beam and the interrogation beam below the surface of the sample;

a non-interferometric detector that detects the returning portion of the interrogation beam;

a polarizing beam splitter, wherein the interrogation beam is configured to pass through the polarizing beam splitter before reaching the sample;

a quarter wave plate configured to guide the returning portion of the interrogation beam to the non-interferometric detector; and a processor configured to calculate an image of the sample based on a detected time-varying intensity modulation of the returning portion of the interrogation beam from below the surface of the sample, wherein the time-varying intensity modulation is caused by the excitation beam focused below the surface of the sample, wherein:

the sample includes tissue;

the excitation beam and the interrogation beam are focused within 1 mm of the surface of the sample;

at least one of the excitation beam and the interrogation beam is focused at a depth greater than 1 µm below the surface of the sample;

the excitation beam and the interrogation beam are confocal; and the system does not include an ultrasound transducer.

21. The NI-PARS of claim 20, further including an additional imaging system selected from fluorescence microscopy, Coherent-Anti-Raman-Stokes microscopy, Raman microscopy, and optical coherence tomography.

\* \* \* \* \*